United States Patent
Jacobi

(10) Patent No.: US 10,667,881 B2
(45) Date of Patent: Jun. 2, 2020

(54) METHOD AND APPARATUS FOR CONTROLLING A SURGICAL LIGHT

(71) Applicant: Berchtold Holding GmbH, Tuttlingen (DE)

(72) Inventor: Leif Jacobi, Tuttlingen (DE)

(*) Notice: Subject to any disclaimer, the term of this patent is extended or adjusted under 35 U.S.C. 154(b) by 240 days.

(21) Appl. No.: 15/140,355

(22) Filed: Apr. 27, 2016

(65) Prior Publication Data

US 2016/0317244 A1   Nov. 3, 2016

(30) Foreign Application Priority Data

Apr. 28, 2015 (DE) ........................ 10 2015 106 519

(51) Int. Cl.
*A61B 90/30* (2016.01)
*H05B 47/105* (2020.01)
*A61B 90/00* (2016.01)

(52) U.S. Cl.
CPC ............ *A61B 90/30* (2016.02); *A61B 90/361* (2016.02); *H05B 47/105* (2020.01); *A61B 2090/308* (2016.02); *A61B 2090/3937* (2016.02); *A61B 2560/0223* (2013.01)

(58) Field of Classification Search
CPC . Y10S 362/804; Y10S 362/802; A61B 90/30; A61B 2017/00398; A61B 2034/2055; A61B 2034/2057; A61B 2034/2068
USPC ........................................ 362/572, 573, 804
See application file for complete search history.

(56) References Cited

U.S. PATENT DOCUMENTS

| 4,884,008 A * | 11/1989 | Bossler .................... F21V 14/04 362/804 |
| 5,038,261 A | 8/1991 | Kloos |
| 7,706,683 B2 * | 4/2010 | Rossner ................. A61B 90/35 396/429 |
| 8,172,751 B2 * | 5/2012 | Kusner .................. A61B 90/30 362/804 |
| 2007/0258243 A1 * | 11/2007 | Segall .................... H05B 37/02 362/276 |
| 2009/0318772 A1 | 12/2009 | Marka et al. |
| 2011/0037840 A1 | 2/2011 | Hiltl et al. |
| 2014/0046341 A1 | 2/2014 | DiCarlo |
| 2015/0282735 A1 * | 10/2015 | Rossner ................. A61B 5/064 600/424 |

FOREIGN PATENT DOCUMENTS

| DE | 20316756 U1 | 4/2005 |
| DE | 102008019191 A1 | 10/2009 |
| DE | 102008039791 A1 | 3/2010 |
| DE | 102009037316 A1 | 2/2011 |
| DE | 10 2011 007 201 A1 | 5/2012 |
| EP | 0299196 A2 | 1/1989 |

(Continued)

OTHER PUBLICATIONS

Extended Search Report dated Oct. 17, 2016 received by the EP Patent Office for EP Application No. EP 16 16 7146.6, 4 pages.

(Continued)

*Primary Examiner* — William J Carter

(57) ABSTRACT

In a method for controlling a surgical light, the luminance distribution is determined spatially selectively in a measured field and the illuminated field size is adapted to the size of the surgical field while taking account of the luminance distribution.

22 Claims, 2 Drawing Sheets

(56) References Cited

FOREIGN PATENT DOCUMENTS

Figure 1:
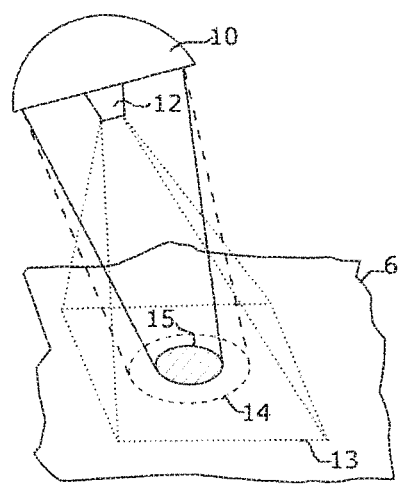

| EP | 0422331 | A2 | 4/1991 |
|----|---------|----|--------|
| EP | 1342947 | A2 | 9/2003 |
| EP | 2136129 | A1 | 12/2009 |
| EP | 2215987 | A1 | 2/2010 |
| WO | 2014016104 | A1 | 1/2014 |

OTHER PUBLICATIONS

Search Report dated Feb. 2, 2016 received by the EP Patent Office for EP Application No. 10 2015 106 519.3, 8 pages.
Related German Search Report dated Apr. 13, 2018 from European Patent Office (six pages).

* cited by examiner

METHOD AND APPARATUS FOR CONTROLLING A SURGICAL LIGHT

The present invention relates to a method and to an apparatus for controlling a surgical light illuminating a surgical field.

The setting of the correct brightness is very important when illuminating a surgical field. It is known from the prior art for this purpose to measure the distance between the surgical light and the surgical field and to keep the intensity of illumination constant in dependence on the distance. It is also known to carry out a luminance measurement and to adapt the brightness of the surgical light accordingly. Keeping the size of the illuminated field constant by focusing in dependence on a measured distance is likewise known from the prior art.

On the use of known surgical lights, an excessive illumination of the area around the actual surgical field covered by sheets or other covers can arise with an incorrectly set illuminated field size. A bright environment is hereby produced to which the surgeon adapts, whereby the actual surgical field appears even darker. Furthermore, inadmissibly high luminance differences in the visual field of the surgeon can result in negative physiological and psychological effects which can impair the visual comfort and the visual performance.

It is the object of the present invention to provide a method and an apparatus for controlling a surgical light illuminating a surgical field with which an optimized setting of the light intensity can take place independently of the distance of the surgical light from the surgical field.

This object is satisfied by the features of the independent claims.

The method in accordance with the invention comprises the following steps in the named order: First, a spatially selective determination of the luminance distribution is carried out in a measured field which is larger than a maximum illuminated field size of the surgical light. The maximum illuminated field size of the surgical light can be changed, for example, by focusing or by controlling individual illuminants within the surgical light, i.e. the maximum illuminated field size of the surgical light is known. A measured field can accordingly be selected which is larger than the maximum illuminated field size and the luminance distribution within this measured field can be determined spatially selectively, i.e. with spatial resolution.

A conclusion can be drawn on the actual size of the surgical field from the determined luminance distribution such that, in a second step, the illuminated field size of the surgical light can be adapted to the size of the surgical field determined in the first step while taking account of the luminance distribution. The illuminated field size can therefore be increased or decreased in the second step such that the illuminated field generated is adapted to the size of the surgical field, i.e. substantially corresponds to the size of the surgical field.

Subsequently, in a third step, the light intensity of the surgical light can be set while taking account of the luminance of the environment of the surgical field within the measured field. The light intensity of the surgical light can be adapted such that the luminance ratio between the surgical field and the environment of the surgical field is optimized. If, for example, the environment of the surgical field is very weakly reflective, the light intensity of the surgical light can be set higher. If the environment is highly reflective, the light intensity can be set lower to avoid glare effects. A setting of the light intensity of the surgical light therefore takes place while taking account of the luminance of the environment of the surgical field disposed in the measured field.

Advantageous embodiments of the invention are described in the description, in the drawing and in the dependent claims.

In accordance with a first advantageous embodiment, a luminance object which corresponds to the surgical field can be determined from the determined luminance distribution. A luminance object whose outer contour corresponds to the outer contour of the surgical field can namely be defined by means of known processes, for example, the gradient process, due to the spatially selective measurement of the luminance. The luminance object determined in this manner can then be used further to carry out the adaptation of the illuminated field size of the surgical light.

The setting of a desired light intensity adapted to the environment of the surgical field can take place in different manners. In each case, the light intensity is adapted such that it is optimized for the surgeon in dependence on the brightness of the environment of the surgical field. In accordance with an advantageous embodiment, a family of characteristics can be used for setting the light intensity in which light intensities are stored in dependence on the size of the surgical field and on the brightness of the environment of the surgical field. Since the brightness in the environment of the surgical field and also the light field size are known, an optimized brightness value which has been empirically determined, for example, can be read out of the family of characteristics.

Alternatively or additionally, a ratio between the luminance in the surgical field and the luminance in the environment of the surgical field can be predefined for setting the adapted light intensity, with the predefined ratio in particular being able to vary with the size of the illuminated field. It is thus possible, for example, to predefine that the luminance within the surgical field is always higher by a specific percentage than the luminance in the environment of the surgical field. It can also be predefined, for example, that the luminance is lower with a smaller surgical field and higher with a larger surgical field or that the luminance is higher with a smaller surgical field and lower with a larger surgical field.

In accordance with a further advantageous embodiment, an illuminated field size which inscribes the luminance object can be calculated from a determined luminance object. In other words, the geometrical center of the luminance object and its outer contour can be determined and an illuminated field size can be achieved from these data which the previously determined luminance object, i.e. the site of the surgery, completely inscribes.

In accordance with a further advantageous embodiment, the spatially selective determination of the luminance distribution can take place as a selective luminance measurement by means of a plurality of individual sensors. It is alternatively possible to determine the luminance distribution using a calibrated camera, for example a grayscale camera, which is possible in an inexpensive manner. Finally, the use of a luminance camera is also possible.

In accordance with a further advantageous embodiment, at least one reflective mark can be used for a better recognition of the surgical field margin. Such a reflective mark can only be used temporarily and manually, for example, before the actual surgery. In accordance with a further advantageous embodiment, a surgical field cover can be used whose margin is provided with a reflective mark reflecting in the non-visible range (for example in the infrared range or in the near UV range) or in the visible range. Such a surgical field cover as is typically used has an opening with a peripheral margin such that the peripheral margin can be provided with a continuous reflective mark or with a plurality of individual reflective marks, which facilitates the automated detection of the size or contour of the surgical field.

The adaptation of the illuminated field size to the size of the surgical field can generally take place such that the size of the illuminated field is exactly the same size as the extent of the surgical field. In accordance with a further embodiment, however, the illuminated field size can also be set somewhat larger than the size of the surgical field such that the illuminated field covers the outer contour of the surgical field in every case.

In accordance with a further aspect of the present invention, it relates to an apparatus for carrying out a method of the above-described kind, wherein the apparatus comprises a sensor system for a spatially selective determination of the luminance distribution in a measured field. A device for adapting the illuminated field size of a surgical light is furthermore provided and a device for setting the light intensity of the surgical light is configured such that the light intensity can be adapted to the environment of a surgical field within the measured field. This apparatus is preferably integrated into a handle for a surgical light such that already existing surgical lights can be retrofitted with the apparatus. Alternatively, the apparatus can be integrated in a lamp body of the surgical light or in the handle and the lamp body.

Figure 2:
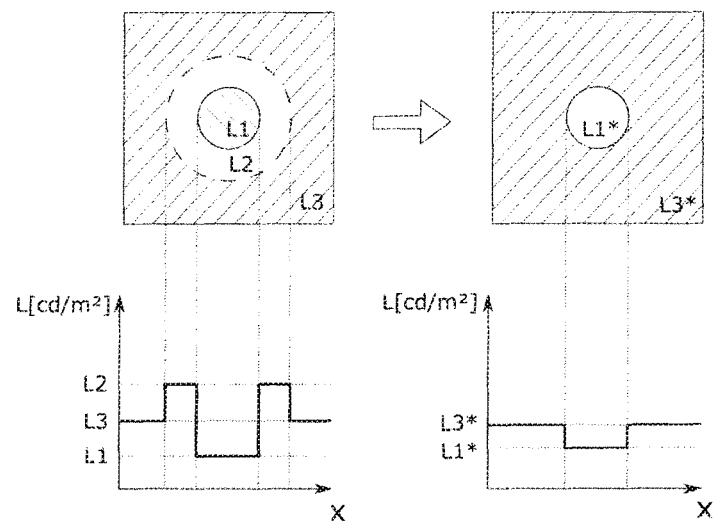
Figure 3:
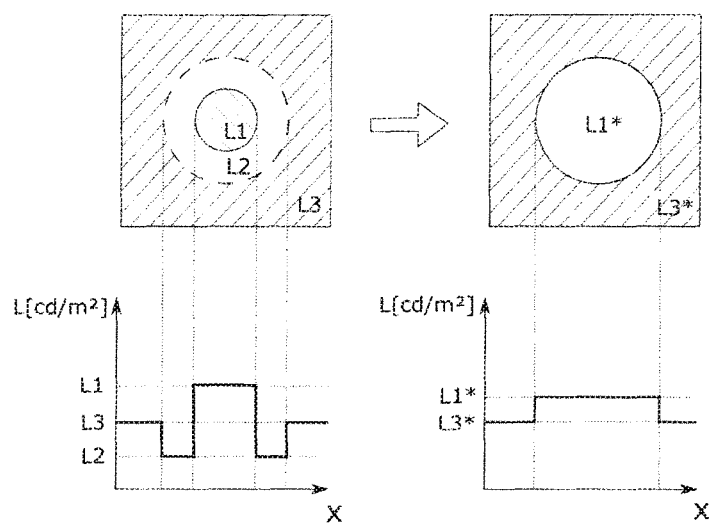
Figure 4:
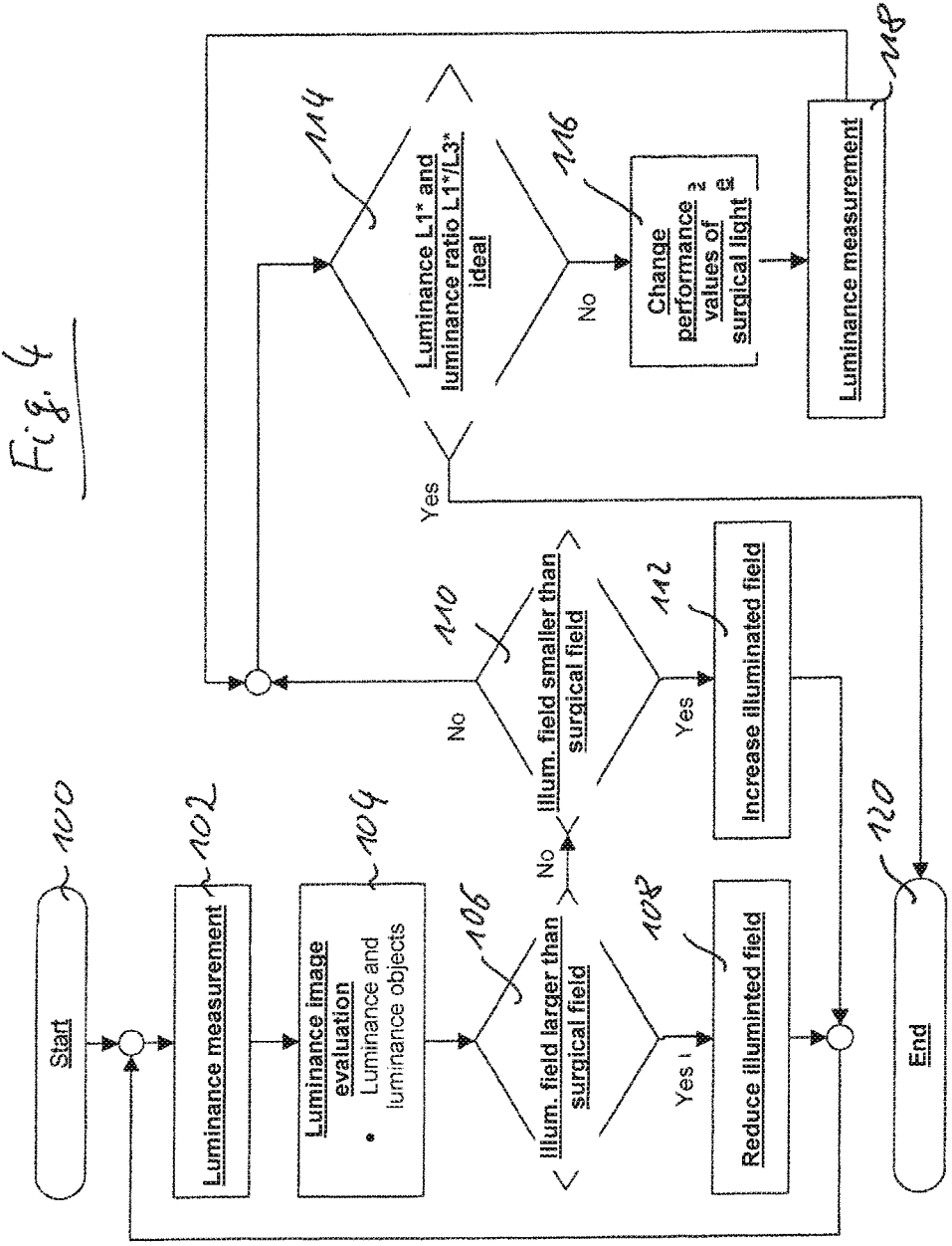

The present invention will be described in the following purely by way of example with reference to an advantageous embodiment and to the enclosed drawings. There are shown:

FIG. 1 a perspective view of a surgical field illuminated by a surgical light;

FIG. 2 and FIG. 3 the adaptation of the illuminated field size to the surgical field; and FIG. 4 a regulation scheme for the setting of the illuminated field size and the regulation of the luminance within the surgical field.

FIG. 1 shows a perspective view of a surgical light 10 which is only shown schematically and in whose central handle 12 measurement means and electronics are provided for the measurement means control, the information processing and the generation of control signals for the light as well as for monitoring control variables. The integration of both the measurement means (sensor system in the form of a camera or in the form of light sensors) and also of the information processing in the form of hardware and software allows a customer-oriented retrofitting of the functions in accordance with the invention. The unit integrated into the handle 12 only transmits control signals to the lamp body, in a similar manner to a lamp operation, to vary the light intensity and the illuminated field size of the surgical light.

As FIG. 1 illustrates, the surgical light 10 illuminates a surgical field 15 with a preselected illuminated field size 14 which is shown dashed and which is larger than the actual surgical field 15 so that the environment of the surgical field 15 is also illuminated in an annular strip.

A sensor system, preferably a luminance camera, provided within the handle 12 serves for detecting brightness differences at different positions in the working range of the surgeon and the detected brightness differences can be correlated with the position of the light or at least with the optical axis of the light so that the luminance distribution can be spatially selectively determined in a measured field 13 which is larger than the maximum illuminated field size 14 of the surgical light.

In accordance with the method in accordance with the invention, the illuminated field size of the surgical light is subsequently first adapted to the size of the surgical field 15 while taking account of the determine luminance distribution.

FIG. 2 illustrates the adaptation of the illuminated field size with too large an initial illuminated field. In this respect, a first recording of the luminance in the camera frame takes place first, with the light 10 being aligned to the surgical field (FIG. 2, reference symbol A). Subsequently, the range boundaries or the luminance objects in the frame can be calculated so that the mean luminance values can be calculated in the located ranges L1 (surgical field), L2 (illuminated range) and L3 (environment). The illuminated field size, i.e. the spatial extent of the range with the luminance L2 can then be reduced on the basis of the data thus determined so that the illuminated range subsequently corresponds to the surgical field.

The intensity of illumination can subsequently be varied (FIG. 2, reference symbol B) such that the luminance L1* in the surgical field adopts a value optimized for the visual task and for the present peripheral luminance L3*, with the peripheral luminance L3* likewise being able to be changed by the adaptation of the illuminated field size in a certain range in comparison with L3 before the size adjustment.

The luminance values shown in FIG. 2 are indicated purely by way of example. It is thus also possible that the luminance L1* is larger than the luminance L3*.

FIG. 3 illustrates a situation in which the initial illuminated field L1 is smaller than the surgical field L2. The illuminated field size is also changed here such that it substantially corresponds to the surgical field and the luminance is subsequently set to a value L1* which is optimized with respect to the environmental luminance L3*. In all cases, the method in accordance with the invention is carried out without a distance measurement.

The above method, which can be configured as a control or as a regulation, will be explained again in the following with reference to FIG. 4.

The method begins with step 100 and subsequently carries out a measurement of the luminance in step 102, with an evaluation of the determined luminance image taking place in step 104 and with one or more luminance objects being determined from the luminance distribution. A query is made in the subsequent step 106 whether the illuminated field 14 of the surgical light 10 is larger than the surgical field 15 determined by the found luminance distribution. If this is the case, the illuminated field is reduced in size in the subsequent step 108 and a return to step 102 is made. If this is not the case, a query is made in step 110 whether the illuminated field is smaller than the surgical field 15. If this is the case, the illuminated field is increased in size in step 112 and a return to step 102 is made. If this is not the case, the illuminated field has the size of the surgical field and the light intensity of the surgical light can subsequently be optimized while taking account of the environment of the surgical field. For this purpose, a query is made in step 114 whether the luminance L1* of the now existing illuminated field is at an optimized luminance ratio to the luminance of the environment L3*. If this is the case, the method can be ended in step 120. If this is not the case, the light intensity of the surgical light is changed in step 116 by changing its performance values, i.e. by a regulation of the intensity. The luminance is subsequently again measured in step 118 and a return to step 114 is made.

It is understood that it is also possible, instead of step 120, to return to step 102 or to step 114 in order to achieve a continuous regulation. It is also obvious that the above-described invention cannot only be used with surgical lights, but can also be used in the same manner with any other desired lights such as examination lights and the like.

A separate switch element can be provided at a control of the surgical light for activating the above-described method. It is additionally possible to switch off the automatic intensity adaptation manually at any time. Provision can additionally be made to reduce the brightness of the light and/or to reduce the illuminated field size if it is found, for example, on the basis of the luminance measurement that the light is not oriented in the direction of the surgical field, but rather into space. The dazzling of medical staff is hereby prevented.

The invention claimed is:

1. A method for controlling a surgical light illuminating a surgical field comprising the following steps in the named order:
   a) illuminating the surgical field with the surgical light so that an illuminated field size from the surgical light is larger than the surgical field and so that a portion of an environment adjacent to and surrounding the surgical field is also illuminated;
   b) spatially selectively determining a luminance distribution of a measured field which is larger than a maximum illuminated field size of the surgical light, wherein the luminance distribution of the measured field comprises luminance distributions of the surgical field, the portion of the environment adjacent to and surrounding the surgical field, and a portion of the measured field surrounding the portion of the environment;
   c) determining, based on the luminance distribution of the measured field, a first boundary between the surgical field and the portion of the environment adjacent to and surrounding the surgical field and a second boundary between the portion of the environment and the portion of the measured field surrounding the environment, and adapting the illuminated field size of the surgical light to the size of the surgical field based on the determined first and second boundaries; and
   d) setting a light intensity of the surgical light based on a spatially selectively determined luminance distribution of the environment.

2. The method of claim 1, further comprising the step of determining a luminance object which corresponds to the surgical field from the luminance distribution of the measured field.

3. The method of claim 2, wherein a light field size which inscribes the luminance object is calculated from the luminance object.

4. The method of claim 3, wherein the light field size is circular.

5. The method of claim 1, wherein, for setting the light intensity in step d), a family of characteristics is used in which light intensities are stored in dependence on the size of the surgical field and on the brightness of the environment.

6. The method of claim 1, wherein the spatially selective determination of the luminance distribution takes place as a selective luminance measurement by means of a plurality of individual sensors.

7. The method of claim 1, wherein the luminance distribution is determined using a calibrated grayscale camera.

8. The method of claim 1, wherein at least one reflective mark is used for recognition of the surgical field margin.

9. The method of claim 8, wherein a surgical field cover is used for recognition of the surgical field margin, with the margin of said surgical field cover being provided with a reflective mark reflecting in the non-visible range or in the visible range.

10. The method of claim 1, wherein setting the light intensity of the surgical light is based on a predefined ratio between the luminance in the surgical field and the luminance in the environment, and wherein the ratio varies with the size of the illuminated field.

11. A surgical lighting system comprising:
   at least one illumination source configured to illuminate a surgical field so that an illuminated field from the surgical light is larger than the surgical field and so that a portion of an environment adjacent to and surrounding the surgical field is also illuminated;
   a sensor system configured to spatially selectively determine a luminance distribution of a measured field which is larger than a maximum illuminated field size of the surgical light, wherein the luminance distribution of the measured field comprises luminance distributions of the surgical field, the portion of the environment adjacent to and surrounding the surgical field, and a portion of the measured field surrounding the portion of the environment;
   a control system configured to determine, based on the luminance distribution of the measured field, a first boundary between the surgical field and the portion of the environment adjacent to and surrounding the surgical field and a second boundary between the portion of the environment and the portion of the measured field surrounding the environment, control the at least one illumination source to adapt the illuminated field size of the surgical light to the size of the surgical field based on the determined first and second boundaries, and set a light intensity of the surgical light based on a spatially selectively determined luminance distribution of the environment.

12. A method for controlling a surgical light illuminating a surgical field, the method comprising:
   illuminating the surgical field with the surgical light so that an illuminated field from the surgical light is smaller than the surgical field;
   determining a luminance distribution of a measured field that is larger than a maximum illuminated field size of the surgical light, wherein the luminance distribution of the measured field comprises luminance distributions of the illuminated field, the surgical field, and a portion of the measured field surrounding the surgical field;
   determining, based on the luminance distribution of the measured field, a first boundary between the illuminated field and the surgical field and a second boundary between the surgical field and the portion of the measured field surrounding the surgical field;
   adapting a size of the illuminated field of the surgical light to a size of the surgical field based on the determined first and second boundaries; and
   setting a light intensity of the surgical light based on a luminance distribution of the environment.

13. The method of claim 12, comprising determining a luminance object that corresponds to the surgical field from the luminance distribution of the measured field.

14. The method of claim 13, wherein a light field size that inscribes the luminance object is calculated from the luminance object.

15. The method of claim 14, wherein the light field size is circular.

16. The method of claim 12, wherein, for setting the light intensity, a family of characteristics is used in which light intensities are stored based on the size of the surgical field and on the brightness of the environment.

17. The method of claim 12, wherein determining the luminance distribution comprises determining a selective luminance measurement via a plurality of individual sensors.

18. The method of claim 12, wherein the luminance distribution is determined using a calibrated grayscale camera.

19. The method of claim 12, wherein at least one reflective mark is used for recognition of the first boundary.

20. The method of claim 19, wherein a surgical field cover is used for recognition of the first boundary, with a margin of the surgical field cover comprising a reflective mark reflecting in a non-visible range or in a visible range.

21. The method of claim 12, wherein setting the light intensity of the surgical light is based on a predefined ratio between the luminance in the surgical field and the luminance in the environment, and wherein the ratio varies with the size of the illuminated field.

22. A surgical lighting system comprising:
at least one illumination source configured to illuminate a surgical field so that an illuminated field from the surgical light is smaller than the surgical field;
a sensor system configured to determine a luminance distribution of a measured field that is larger than a maximum illuminated field size of the surgical light, wherein the luminance distribution of the measured field comprises luminance distributions of the illuminated field, the surgical field, and a portion of the measured field surrounding the surgical field;
a control system configured to determine, based on the luminance distribution of the measured field, a first boundary between the illuminated field and the surgical field and a second boundary between the surgical field and the portion of the measured field surrounding the surgical field, control the at least one illumination source to adapt a size of the illuminated field of the surgical light to a size of the surgical field based on the determined first and second boundaries, and set a light intensity of the surgical light based on a luminance distribution of the environment.

* * * * *